United States Patent
Lepper, Jr. et al.

(10) Patent No.: US 6,278,522 B1
(45) Date of Patent: Aug. 21, 2001

(54) OPTICAL FILTER FOR SPECTROSCOPIC MEASUREMENT AND METHOD OF PRODUCING THE OPTICAL FILTER

(75) Inventors: James M. Lepper, Jr., Trabuco Canyon; Mohamed Kheir Diab, Mission Viejo, both of CA (US)

(73) Assignee: Masimo Laboratories, Irvine, CA (US)

( * ) Notice: Subject to any disclaimer, the term of this patent is extended or adjusted under 35 U.S.C. 154(b) by 0 days.

(21) Appl. No.: 09/318,721

(22) Filed: May 26, 1999

Related U.S. Application Data

(60) Continuation of application No. 09/088,397, filed on Jun. 1, 1998, now Pat. No. 5,940,182, which is a division of application No. 08/486,798, filed on Jun. 7, 1995, now Pat. No. 5,760,910.

(51) Int. Cl.[7] ............................. G01N 21/25; G02B 5/22
(52) U.S. Cl. ....................... 356/416; 356/419; 359/888
(58) Field of Search .................. 356/337, 419, 356/416, 417, 317, 318; 258/226, 458.1; 359/588, 359, 589, 580, 590, 584; 427/266, 269, 282, 289, 523, 526, 527, 579, 585

(56) References Cited

U.S. PATENT DOCUMENTS

| | | | |
|---|---|---|---|
| 2,708,389 | 5/1955 | Kavanagh | 359/590 |
| 3,442,572 | 5/1969 | Illsley et al. | 359/578 |
| 3,661,462 * | 5/1972 | Natens | 356/51 |
| 3,771,857 | 11/1973 | Thomasson et al. | 359/587 |
| 3,832,548 * | 8/1974 | Wallack | 250/343 |
| 3,885,879 | 5/1975 | Louder | 356/323 |
| 3,914,464 | 10/1975 | Thomasson et al. | 430/329 |
| 3,929,398 | 12/1975 | Bates | 356/416 |
| 3,981,568 | 9/1976 | Bartolomei | 359/587 |
| 4,054,389 | 10/1977 | Owen | 356/419 |
| 4,187,475 | 2/1980 | Wieder | 372/31 |
| 4,346,992 | 8/1982 | Schwartz | 356/73 |
| 4,901,728 | 2/1990 | Hutchison | 600/316 |
| 4,957,371 | 9/1990 | Pellicori et al. | 356/419 |
| 5,200,855 | 4/1993 | Meredith, Jr. et al. | 359/588 |
| 5,209,231 | 5/1993 | Cote et al. | 600/310 |
| 5,218,473 * | 6/1993 | Seddon et al. | 359/589 |
| 5,398,681 | 3/1995 | Kupershmidt | 600/316 |
| 5,416,325 | 5/1995 | Buontempo et al. | 250/353 |
| 5,416,579 | 5/1995 | Barshad et al. | 356/300 |

FOREIGN PATENT DOCUMENTS

| | | |
|---|---|---|
| 3724852 | 1/1988 | (DE) . |
| 466403 | 1/1992 | (EP) . |
| 61-035681 | 2/1986 | (JP) . |

OTHER PUBLICATIONS

Yang, Shumel, "Circular, Variable, Broad–Bandpass Filters With Induced Transmission at 200–1100nm", *Applied Optics*, vol. 32, No. 25, Sep. 1993, pp. 4836–42.

Squire, J.R., "An Instrument for Measuring the Quantity of Blood and its Degree of Oxygenation in the Web of the Hand", *Clinical Science*, vol. 4, pp. 331–339, 1940.

* cited by examiner

*Primary Examiner*—Frank G. Font
*Assistant Examiner*—Michael P. Stefira
(74) *Attorney, Agent, or Firm*—Knobbe, Martens, Olson & Bear

(57) ABSTRACT

An optical filter used in applications involving spectroscopic measurements is fabricated by depositing layers of optical coatings onto a substrate. The layers are deposited so as to have a substantially constant thickness in a first direction along the surface of the substrate, and a gradually increasing thickness along a direction perpendicular to the first direction. The structure of the optical filter allows for large scale production of the filter so that costs in producing the filter are greatly reduced. The filter may be used in a variety of applications including, but not limited to chemical analysis, blood glucose monitoring, and the like.

3 Claims, 8 Drawing Sheets

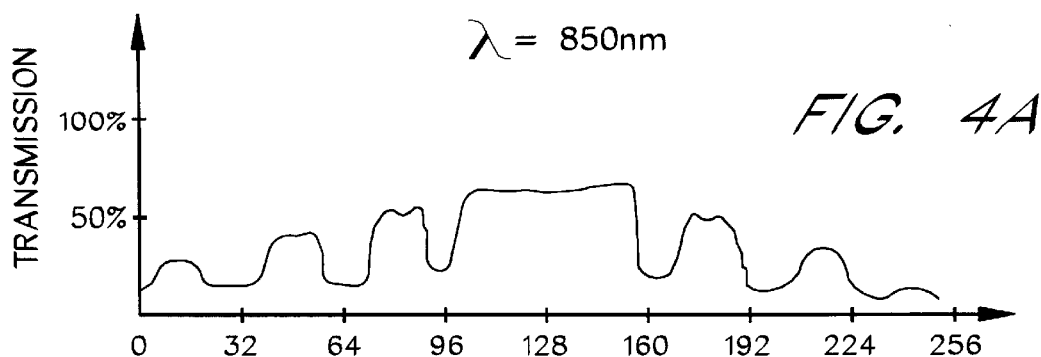
FIG. 4A
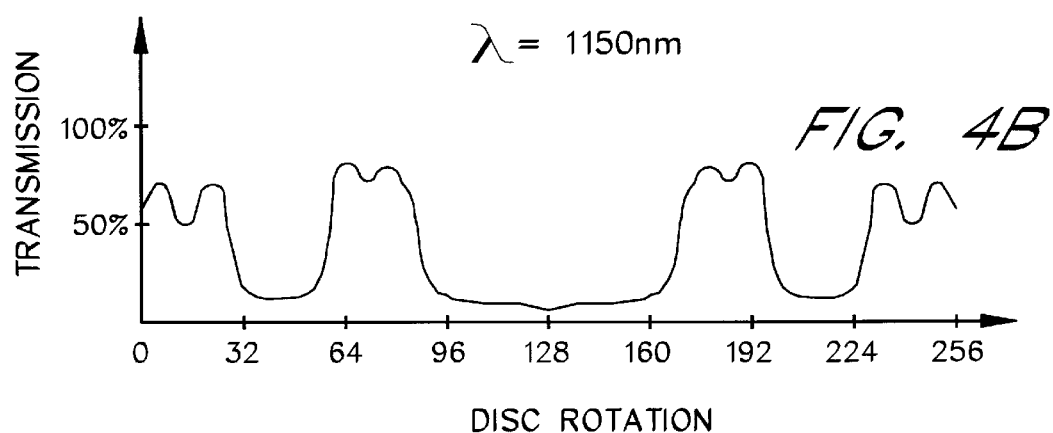
FIG. 4B
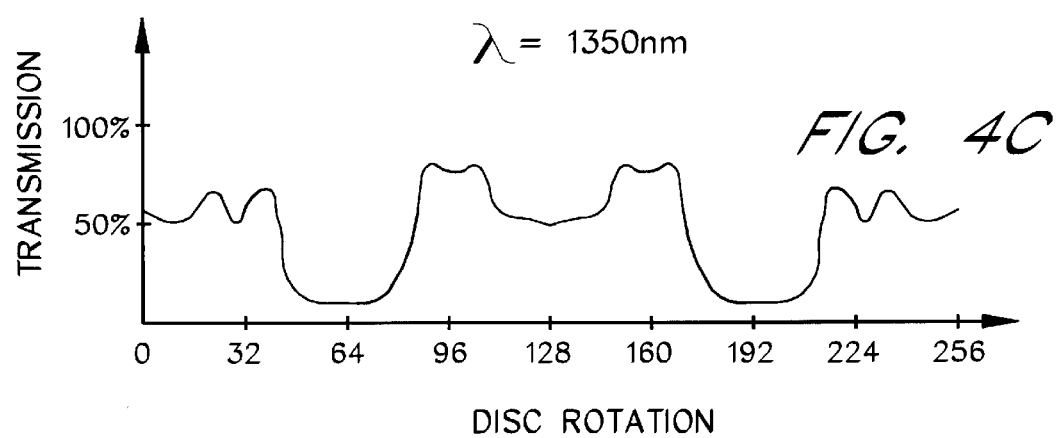
FIG. 4C
$$\begin{bmatrix} f_{\phi_1\lambda_1} & f_{\phi_1\lambda_2} & \cdots & f_{\phi_1\lambda_n} \\ f_{\phi_2\lambda_1} & f_{\phi_2\lambda_2} & & \\ \vdots & & \ddots & \\ f_{\phi_m\lambda_1} & \cdots & & f_{\phi_m\lambda_n} \end{bmatrix}$$
FIG. 4D

1

OPTICAL FILTER FOR SPECTROSCOPIC MEASUREMENT AND METHOD OF PRODUCING THE OPTICAL FILTER

This application is a continuation of prior application Ser. No. 09/088,397, filed Jun. 1, 1998, now U.S. Pat. No. 5,940,182, which is a division of Ser. No. 08/486,798, filed Jun. 7, 1995, now U.S. Pat. No. 5,760,910.

BACKGROUND OF THE INVENTION

1. Field of the Invention

The present invention relates to optical filters which are used in applications where spectroscopic measurements are used to determine the properties of substances such as chemicals and other substances.

2. Description of the Related Art

Optical filters are well known in applications involving spectroscopic measurement. Spectroscopic measurement is used to determine the properties and chemical composition of various substances in a sample based upon the optical characteristics of the sample. In a typical spectroscopic measurement, light (in the visible and non-visible range) is used to illuminate the sample over multiple frequency spectra. More than one optical frequency (wavelength) is used to more precisely determine the optical characteristics of the sample and also to subtract out interference. In some applications, the light reflected from the sample is detected, while in other applications light transmitted through the sample is detected to determine the optical characteristics of the sample. In addition, a combination of the transmission through the sample and the reflections from the filter may be employed.

The detected light is usually quantified to provide an indication of the "frequency response" of the sample at each of the frequency spectra. As is well known in the art, each substance has definable optical properties determined by the frequencies at which the substance reflects and absorbs light. Thus, the optical characteristics of a given substance may be quantified (e.g., plotted as intensity of reflected or transmitted light versus frequency) to provide an indication of the optical characteristics of that substance. Since different substances typically have distinct optical characteristics, quantified measurements of the optical properties of a sample containing several substances can serve as the basis for distinguishing among or making other measurements relating to the several substances within a sample. Precise measurements of the reflected or transmitted light can be used to determine the precise concentration of the various substances within a sample.

Some present spectroscopic measurement systems use multiple light emitting diodes (LEDs) or laser sources to provide light at the desired wavelengths. However, very expensive, high precision wavelength light sources must be employed in order to manufacture such a system with the necessary wavelength accuracy for each of the sources.

One alternative method of generating light at multiple frequencies involves rotating an optical filter between the sample to be measured and a broadband light source. Current optical spectroscopic devices, as identified by the inventor for use in the present invention, often require expensive custom-made filters which are used to generate a pattern of optical signals to be transmitted. One such filter, commonly known as a dichroic filter, comprises a rotating optically coated disk which includes regions of varying optical thickness. As the wheel spins, light from the broadband light source passes through different portions of the wheel so that light of various frequencies are passed by the filter to illuminate the sample. That is, the regions on the dichroic filter are formed in a pattern so that rotation of the optical disk results in the transmission of selected optical bands. In many previous applications involving precise spectroscopic measurement, optical filters have been designed with very high tolerances. Furthermore, the methods for manufacturing such filters have often precluded the possibility of manufacturing the filters by mass production. Thus, even optical filters of this kind may be prohibitively expensive to fabricate.

SUMMARY OF THE INVENTION

The present invention provides a rotating dichroic filter for spectroscopic measurement wherein the cost of the filter is approximately 100 times less than conventional rotating dichroic filters. This is accomplished by first relaxing the specifications of the filter and compensating for the relaxation of filter specifications through more intensive signal processing steps. In addition, the filter is constructed in a manner which allows for easier production. The filter constructed in accordance with the present invention allows from 10 to 100 times as much light to pass while maintaining the necessary precision through signal processing.

One aspect of the present invention involves a method of manufacturing an optical filter. The method involves a number of steps. An optical substrate is provided having a top surface and a bottom surface, and layers of optical coating are deposited on the top surface such that the layers vary in thickness across the top of the substrate in a first direction. The thickness of the layers is substantially constant in a second direction substantially perpendicular to the first direction. In one embodiment, the method further involves creating a mounting hole in the center of the substrate. In addition, an opaque strip along at least a portion of the substrate is deposited in one embodiment.

Another aspect of the present invention involves an optical filter. The optical filter has a substrate having a top surface and a bottom surface. The filter also has a plurality of optical coatings deposited on the top surface of the substrate such that the coatings vary in thickness in a first direction across the top surface. The coatings are substantially constant in thickness across the top surface in a second direction substantially perpendicular to the first direction.

Another aspect of the present invention comprises an optical filter having a generally circular substrate. Layers of optical coatings deposited on the substrate provide a non-imaging interferometer wherein approximately one-half of light incident upon the coatings passes through the coatings over the entire surface of the substrate.

Yet another aspect of the present invention involves an optical filter. A substrate having a top surface and a bottom surface has a plurality of layers of optical coatings varying in thickness in a first direction across the substrate. The layers provide optical transmission characteristics for the optical filter to provide an optical filter which transmits more than one wavelength through the filter at all locations across the surface of the filter.

BRIEF DESCRIPTION OF THE DRAWINGS

FIGS. 4A–4C depict in graph form the optical transmission characteristics for an exemplary dichroic filter over different degrees of rotation in accordance with the present invention.

FIG. 4D illustrates a matrix used to specify the optical characteristics of an exemplary dichroic filter in accordance with the present invention.

DETAILED DESCRIPTION OF THE INVENTION

Figure 1:
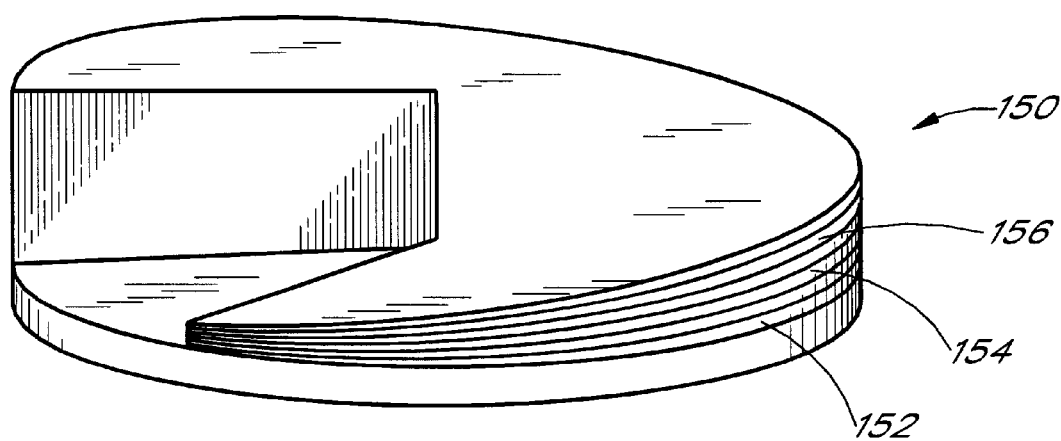
FIG. 1 depicts an exemplary dichroic filter as constructed by conventional methods.

FIG. 1 shows an exemplary dichroic filter fabricated according to conventional methods. Previous methods employed to fabricate such optical filters typically involved laying out a circular substrate and then selectively increasing the coating thicknesses on the surface of the circular substrate as the substrate is rotated with uniform speed.

Such a filter 150 is depicted in FIG. 1 as having coating layers 152, 154, 156, etc., of increasing thicknesses to form a spiral configuration as the filter 150 is rotated. Of course, it should be understood that the coating thicknesses depicted in FIG. 1 are exaggerated for ease of illustration. This method of optical coating is carried around substantially the entire circumference of the circular substrate so that as the coated substrate revolves, the thickness of the optical coating grows throughout the entire revolution and then suddenly drops back from the thickest coating to the thinnest coating at the end of one revolution.

It has been found, however, that such methods of optical coating require high precision and are extremely costly. Furthermore, manufacturing these filters is typically carried out one-by-one, since production methods do not allow for laying out several disks on a single sheet for mass production purposes.

Figure 5:
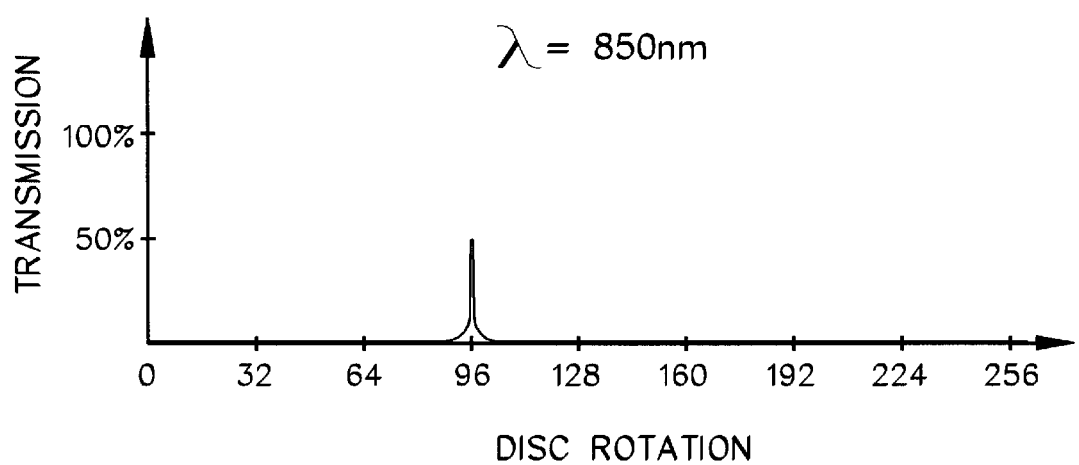
FIG. 5 depicts in graph form the optical transmission characteristics of an exemplary conventional dichroic filter over different degrees of rotation in accordance with the present invention.

In addition, conventional filters of the type depicted in FIG. 1 generally have many layers (e.g., 100 or more layers is common). The number of layers in conventional filters are provided to provide very precise pass bands (for a bandpass filter). FIG. 5 depicts an exemplary transmission characteristic for a conventional rotational dichroic filter versus degrees of rotation for a selected wavelength. As illustrated in FIG. 5, the pass band of the filter is very precise for the selected wavelength, generally without side-lobes, and also provides essentially zero transmission outside the pass band. A very high number of layers is required to obtain a filter with this near ideal precision. It should be understood, that this very narrow passband is in different rotational positions for different wavelengths. In other words, a conventional dichroic filter can be characterized as a monochrometer which passes a different wavelength at different rotational positions.

Creating each layer is expensive due to the continuous rotational variation from thin to thicker. Thus, when many layers are created (e.g., 100 or more for good precision), such conventional filters are very costly.

Figure 2:
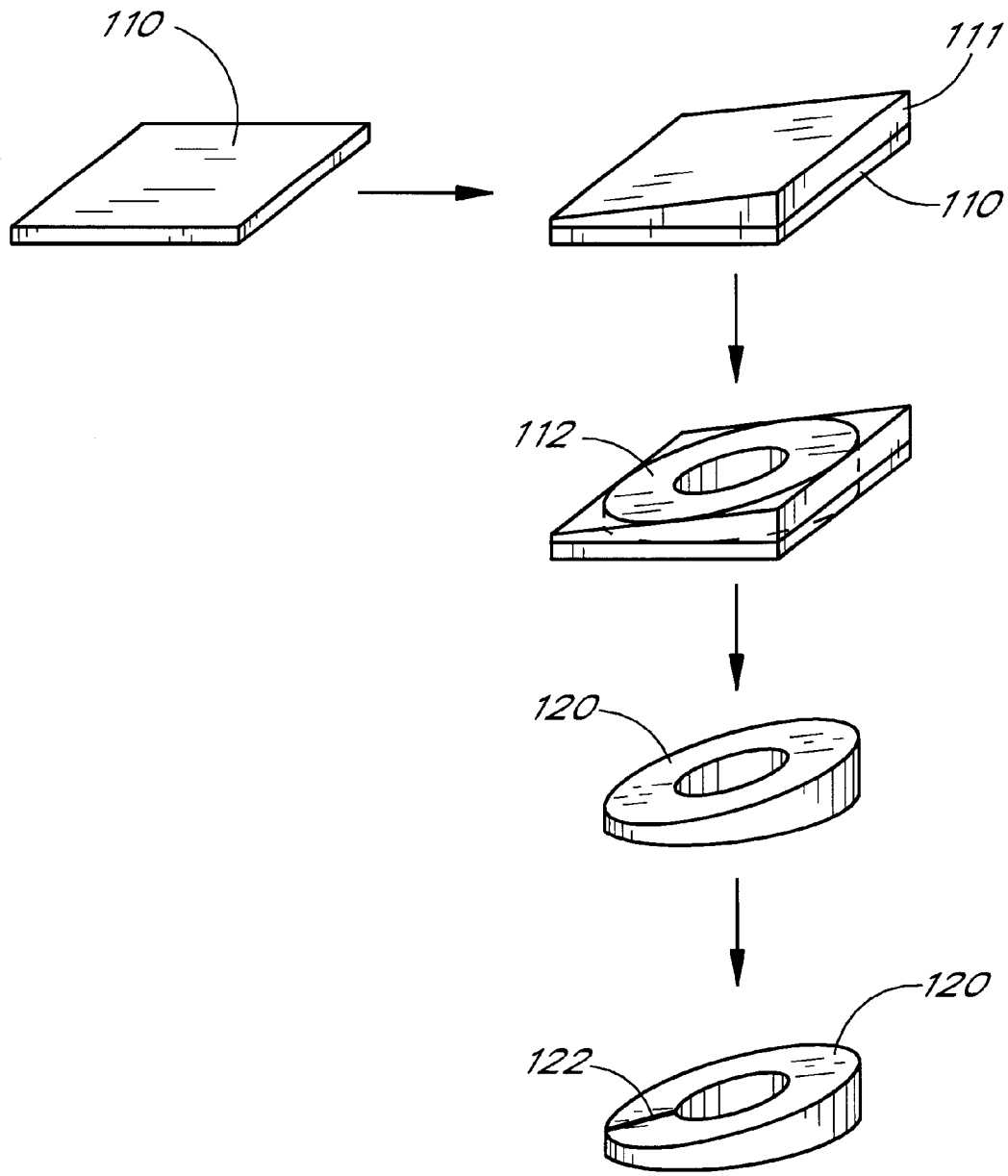
FIG. 2 depicts schematically the general method used in accordance with the present invention to manufacture a rotational optical filter.

In accordance with the present invention, a dichroic filter is disclosed which differs significantly from conventional dichroic filters. FIG. 2 depicts a filter 120 along with the steps followed in the method of producing a filter in accordance with the teachings of the present invention.

The dichroic filter according to the present invention is made in a novel manner in which the multiple optical coatings are created on a substrate to form a wedge-like substrate. For a rotational filter, the substrate is then cut to form a rotational disk filter.

In addition, according to one aspect of the present invention, the dichroic filter has fewer layers than conventional filters. This provides for less precision in the transmission characteristic of the filter. FIGS. 4A–4C depict the optical transmission characteristics for selected wavelengths of an exemplary rotational filter made in accordance with the present invention having only 17 optical coating layers. As illustrated in FIGS. 4A–4C, the transmission characteristic is not as precise as the transmission characteristic of the filter represented in FIG. 5. As depicted in FIGS. 4A–4C, the dichroic filter of the present invention has several pass-bands for each wavelength depicted. In addition, outside the pass-bands, the transmission does not fall completely to zero, as with the conventional precision filters. The reduced precision in the passbands is due to the reduced number of layers in the filter. It should be understood, that the reduced precision explained above is not limited to rotational dichroic filters, but could also be advantageous with dichroic filters that are vibrated (e.g., through oscillation or the like), and for any other optical filter which conventionally involves high precision in the pass-bands. The decreased precision of the filter of the present invention is accommodated with signal processing as further explained below to obtain the required precision. In this manner, the cost of the filter can be reduced.

When both aspects of the filter in accordance with the present invention are used (layering process and reduced number of layers), the resulting filter is much less expensive to construct than conventional dichroic filters. However, it should be noted that using either aspect of reducing cost is advantageous in itself. For instance, a conventional rotational filter could be fabricated with far fewer layers, but using conventional layering techniques such that the filter increases in thickness through the entire revolution of the filter. Alternatively, the method of fabrication disclosed herein could be used to form a rotational filter with conventional precision (e.g., many layers) at reduced manufacturing costs due to the improved manufacturing method.

In the method which reduces the cost of layering the optical filter, a flat substrate 110 (FIG. 2) is coated with optical coatings of increasing thickness to form a wedge-shaped coated layer 111. It should be noted that for purposes of clearly illustrating the present invention, the thickness of the optical coating 111 has been exaggerated, and in practical applications the thickness of the optical layer 111 varies from roughly 1.66 micrometers to about 3.33 micrometers, with an average thickness of about 2.35 micrometers. It should also be understood that these thicknesses are approximate and may vary depending upon the index of refraction of the layer materials. Therefore, in accordance with one aspect of the present invention, the optical coatings which define the filter are applied across a substrate rather than continually applying coatings circumferentially, thus, significantly reducing the cost of the filter. The filter at this point provides a dichroic filter which could be used in oscillating filter type applications.

For a rotational filter, once the optical layers 111 have been applied to the substrate 111, a cylindrical portion 112 is cut from the wedge-shaped slab formed by the optical layer 111 together with the substrate 110. A cylindrical aperture is then formed in the center of the cylindrical portion 112 to form a mounting hole. In certain applications, it is desirable to form an optically opaque strip such as a brass strip 122 over a portion of the optical filter disk 120. The brass strip provides a zero-transmission reference portion of the disc 120 which may be helpful for noise cancellation in certain signal processing applications.

The above description provides ease of illustration for understanding one aspect of the present invention. However, it should be understood that the method may, in practice, involve first cutting the substrate into a disk. Thereafter, the optical coatings are applied onto the disk as though the disk were still square so that the excess falls onto the platform (not shown) supporting the disk within the vacuum tank. In this manner the wedge is formed on the surface of the disk 120 as shown in FIG. 10.

It will be understood that the disk 120 does not continually increase in thickness through the entire circumference of the wheel, but increases in thickness and then decreases in thickness. However, both halves of the circumference can be utilized as further described below.

In addition to the reduced manufacturing cost of the filter described above, in accordance with a further aspect of the present invention, a minimal number of optical coating layers are deposited. In one preferred embodiment, only 17 layers are necessary to obtain the desired resolution.

Although reducing the number of layers results in less precise filters, such imperfections can be accommodated in digital signal processing steps. For example, as explained above, conventional dichroic filters typically pass a single frequency band at a time (FIG. 5), while the filter of the preferred embodiment may allow for multiple bands to pass, since this is accounted for, and can be compensated through signal processing.

It should be noted here that the resolution typically necessary for applications involving more expensive interferometers or monochrometers is typically not necessary for analyzing liquids. However, additional layers can be added at greater spacing intervals in order to increase resolution of the filter.

COMPENSATING DIGITAL SIGNAL PROCESSING

As briefly set forth above, the imprecision of a filter made in accordance with the present invention having a minimal number of optical coatings can be accommodated through signal processing.

Figure 6:
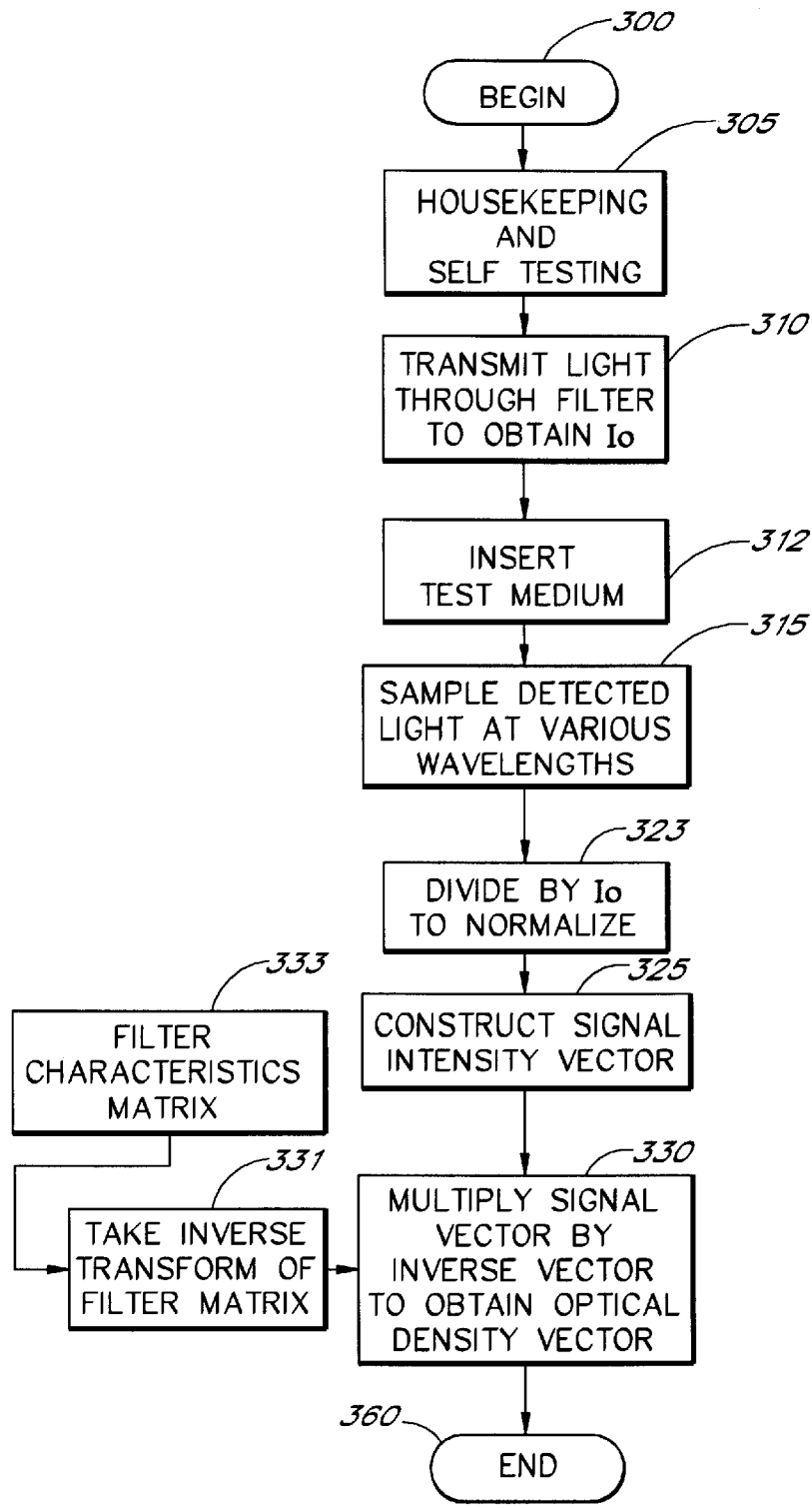
FIG. 6 depicts a general flow chart of the signal processing operations which are used to compensate for the lower optical tolerances of the filter of the present invention.

FIG. 6 is a data flow diagram which details the method used to compensate for the imprecision of the filter made in accordance with the present invention. It should be understood, however, that prior to run-time, initialization is performed.

PRE-RUN-TIME INITIALIZATION

The initialization is performed at the factory or others time prior to use. In general, a filter characteristics matrix is constructed, as described in greater detail below with reference to FIG. 7. The filter characteristics matrix represents the transmission characteristics of the dichroic filter 120 at different portions of the filter 120 and for various wavelengths of light. The filter characteristics matrix is used in order to extract portions of the electrical signal generated by a detector which are due simply to the optical attenuation caused by the filter 120. In other words, by knowing the filter characteristics, the impression of the filter can be accounted for.

The filter characteristic matrix is a two-dimensional matrix. The filter characteristic matrix includes one column for each wavelength of light which is characterized and one row for each position (rotational in the present invention) of the filter 120, at which characterization (of the filter characteristic) is performed. Thus, in one embodiment, the filter characteristic matrix includes 16 columns and 256 rows when 16 wavelengths are characterized and 256 positions of the filter 120 are defined. It should be understood here that it is not necessary that 16 different wavelengths be used; the use of additional wavelengths is particularly advantageous for increasing the signal-to-noise ratio. Since about half of the incident light is transmitted through the filter at each position of the filter, the same wavelength is detected multiple times (although in a unique combination with other wavelengths each time) so that the overall signal intensity is from 10 to 100 times the intensity of any single wavelength and much higher than the noise floor. This is commonly referred to as Felgate's advantage. In this manner the spectral response of the entire filter 120 over the expected measured wavelengths is completely characterized. The method employed to construct the filter characteristics matrix is described in detail below with reference to FIG. 7.

DERIVATION OF THE FILTER CHARACTERISTIC MATRIX

Figure 7:
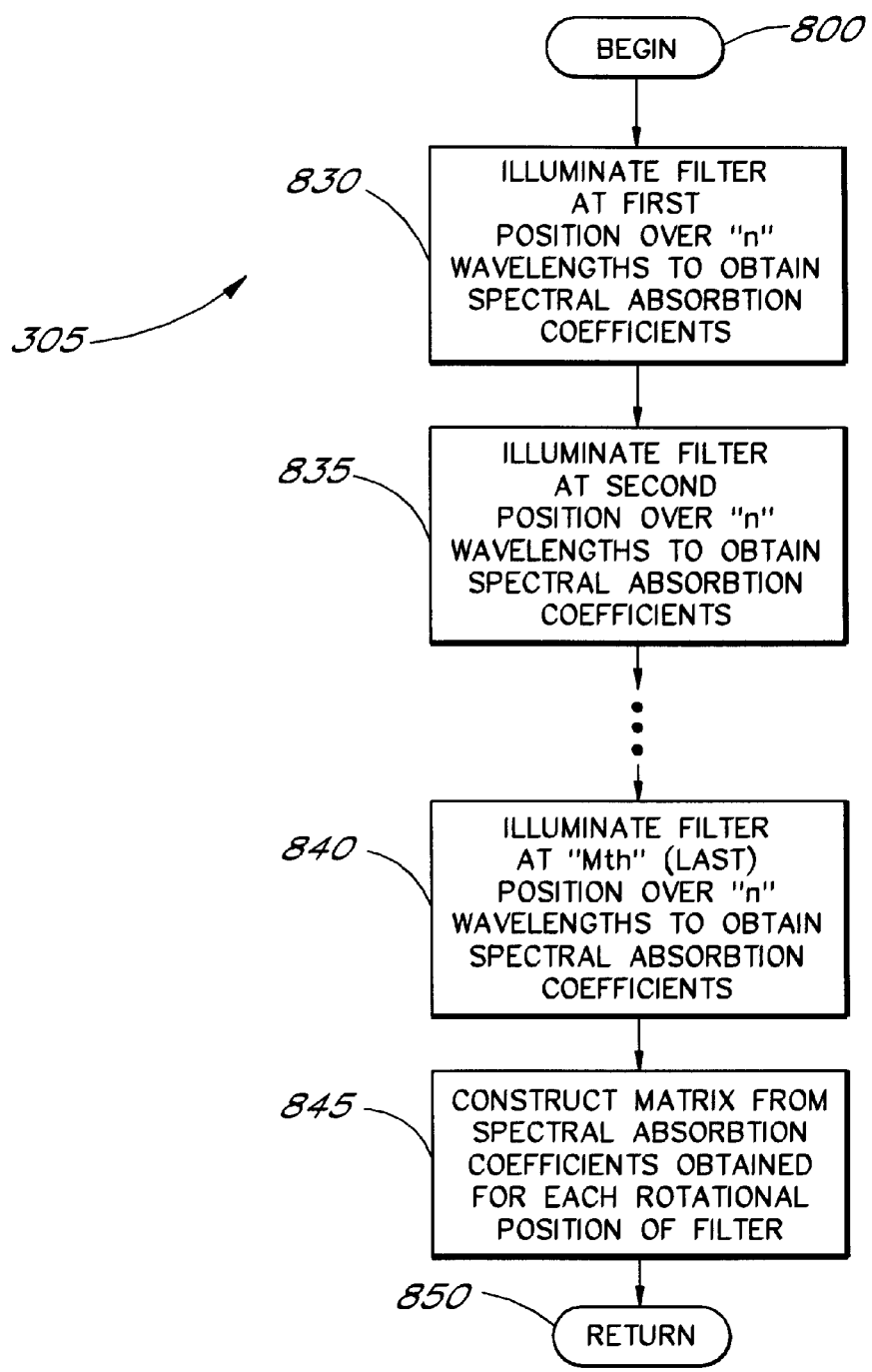
FIG. 7 illustrates a flow chart which sets forth the general steps of obtaining the optical characteristics matrix of FIG. 4D.

FIGS. 4A–4D, together with FIG. 7, illustrate in greater detail, the method employed to obtain the filter characteristic matrix. The derivation routine is illustrated in FIG. 7 and starts with a begin block 800.

The activity blocks 830–845, together with FIGS. 4A–4D, illustrate the method used in accordance with the present invention to construct the filter characteristics matrix. The filter 120 reflects and transmits optical radiation in different proportions for different wavelengths at different places on the filter disk 120. This is clearly illustrated in FIGS. 4A–4C, wherein FIG. 4A represents the optical transmission of light at a wavelength of 850 nanometers plotted versus each of a possible 256 disk rotational positions (for one embodiment). As shown in FIG. 4A, when the disk 120 is in the initial starting position (i.e., $\phi=0$ where 0 represents the rotational position of the filter 120), the transmission of light at 850 nanometers is approximately 10% through the filter 120, while when the disk 120 is rotated so that $\phi=32$, the optical transmission of light at 850 nanometers through the filter 120 is approximately 25%. Again, between the disk rotational positions of $\phi=128$ to $\phi=160$, the transmission of light at 850 nanometers wavelength through the filter 120 is approximately 75%. Thus, the optical transmission for $\lambda=850$ nanometers is entirely characterized over 256 rotational positions of the disk filter 120, as depicted in FIG. 4A.

FIG. 4B depicts the optical transmission characteristics of light at 1,150 nanometers over the same 256 rotational positions of the disk 120. Similarly, FIG. 4C depicts a plot of the optical transmission of light at 1,350 nanometers through the disk filter 120 at each of the 256 rotational positions of the disk 120. In one actual embodiment of the invention, the optical transmission characteristics of the filter 120 are described for 256 rotational positions at each of 16 wavelengths between 850 nanometers and 1,400 nanometers.

Thus, from these measurements, a filter characteristic matrix may be constructed, as shown in FIG. 4D. The filter characteristic matrix designated in FIG. 4D as $F(\phi,\lambda)$ includes 256 rows and 16 columns. Each column of the filter characteristic matrix comprises the spectral transmission characteristics of the disk 120 at each of the 256 rotational positions of the disk 120 for the selected wavelength for that column.

In order to construct the filter characteristic matrix depicted in FIG. 4D, the filter 120 is illuminated at a first rotational position over each of the 16 wavelengths to obtain spectral transmission coefficients for each of the 16 wavelengths, as indicated within an activity block 830. Once the spectral transmission coefficients have been determined for the first rotational position as indicated within the activity block 830, the filter is illuminated at a second rotational position (i.e., $\phi=1$) over the 16 selected wavelengths to obtain spectral transmission coefficients for the second rotational position, as represented in an activity block 835. This method is carried on for each of the possible rotational positions of the disk 120 until, as indicated within an activity block 840, the filter is illuminated at the "mth," or last, rotational position (i.e., position 256) of the disk filter 120 over the 16 selected wavelengths to obtain the spectral transmission coefficients for the last rotational position. In one preferred embodiment, where a stepper motor is used, the rotational positions will be precise from revolution to revolution of the disk 120. Of course, a computer disc motor with salient poles and run at a constant speed could be used provided that phase dithers are minimized to less than one part in 256.

Once spectral transmission coefficients have been determined for all 16 wavelengths of all 256 rotational positions of the disk 120, the filter characteristics matrix is constructed, as indicated within an activity block 845. The matrix defined by column and row where columns represent coeffluents and row represents the wavelength by putting coefficients. Once the filter characteristics matrix is constructed, the system has the necessary constraints for processing.

It should be understood that derivation of a filter characteristic matrix has been described for purposes of the rotational filter 120. However, an oscillating filter, or any filter with defined positions on the filter such as Fabry-Perot type filters and even fixed filters such as those used in CCD applications can also be characterized in accordance with the discussion above.

RUN-TIME PROCESSING

Figure 3:
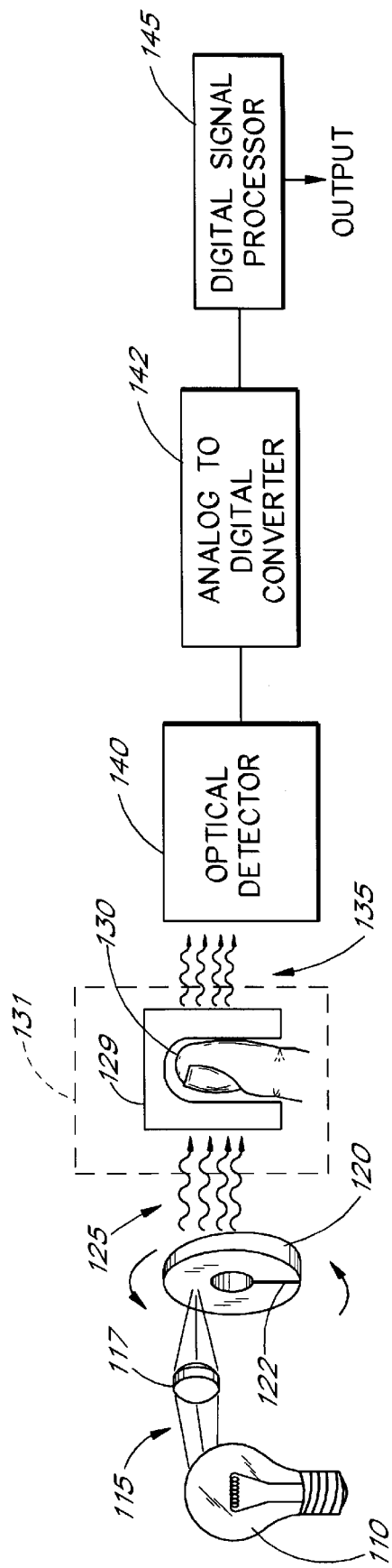
FIG. 3 depicts the dichroic filter of the present invention depicted in FIG. 2 in a blood glucose monitoring application.
Figure 8:
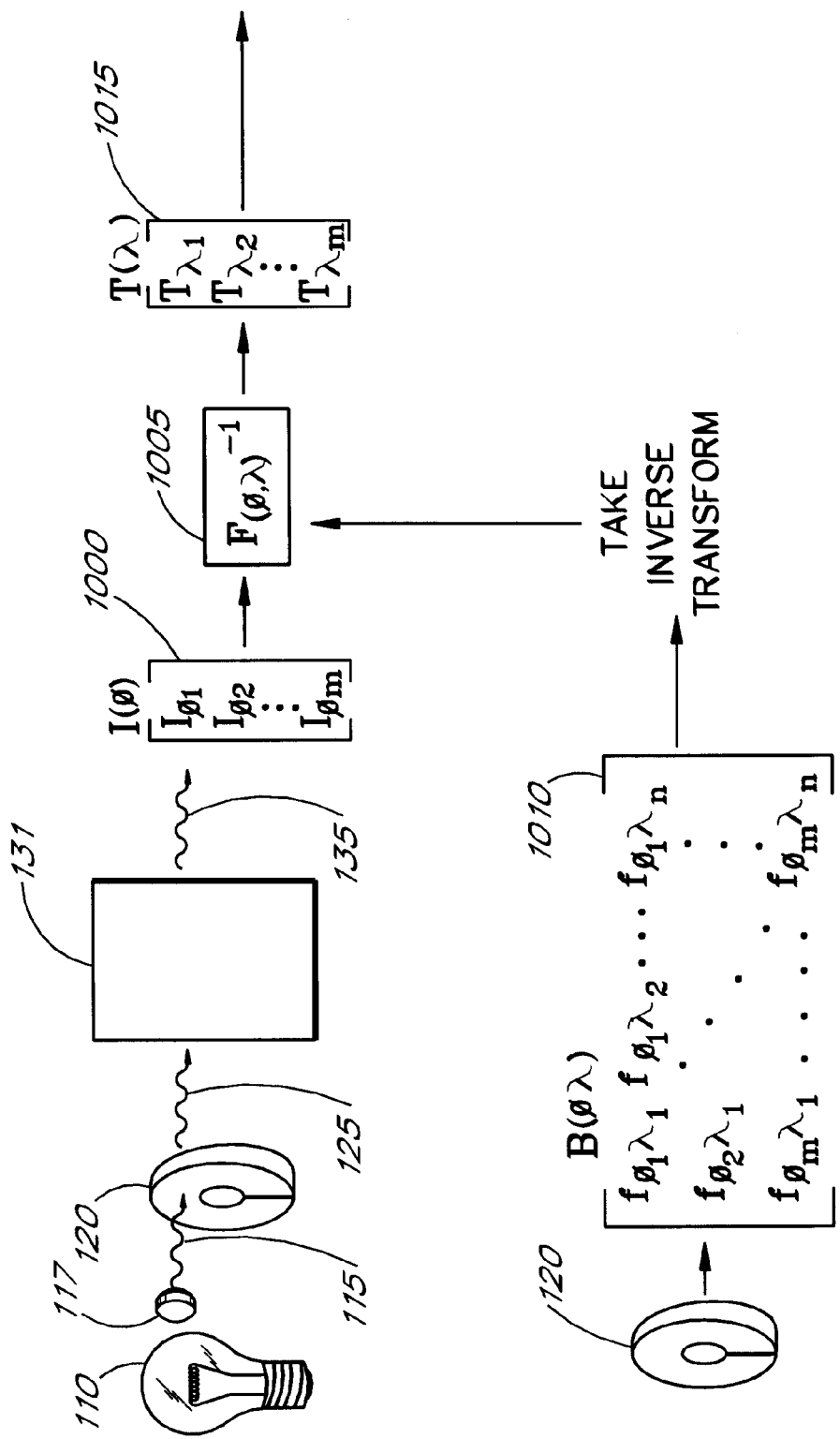
FIG. 8 represents a functional block diagram of the general steps of using the filter of the present invention in conjunction with signal processing to accommodate imprecision.

Discussion of the overall processing in accordance with the present invention in order to account for impression of the filter through the use of the filter characterization matrix is made with reference to FIGS. 3, 6, and 8.

FIG. 3 illustrates the use of the filter 120 in a system for monitoring blood constituents. FIG. 6 illustrates a general flow diagram for the steps of accounting for the imprecision in the filter to obtain the characteristics of a medium under test. FIG. 8 illustrates a general functional diagram of the process of accounting for filter imprecision through signal processing. As depicted in FIG. 6, the start of processing is represented in a begin block 300. First, housekeeping and self-testing procedures are performed, as represented in an activity block 305. Briefly, housekeeping and self testing involves boot operations and conventional initialization a self testing. For example, the system first determines if there is a sufficient signal intensity to take an accurate reading. After housekeeping and self testing is completed, the light source 110 (FIGS. 3 and 8) is activated to transmit light 115 through the filter 120, as represented in an activity block 310. Initially, the light source 110 is activated while no test medium 131 is interposed between the filter 120 and the detector 140. Thus, the light which is detected by a detector 140 (FIG. 3) represents a baseline light intensity ($I_o$) which can be used as a test to insure that a bulb which is too dim or too bright is not inserted as a replacement bulb for example. In one embodiment, a lens 117 (FIG. 8) can be provided between the light source and the filter 120 to provide focused light 115 on the filter 120.

Once the initial baseline light intensity constant has been determined, the medium 131 under test is inserted as indicated in an activity block 312.

As indicated within an activity block 315, the light which is incident upon the detector 140 is converted to an electrical signal and this signal is amplified in a pre-amp (not shown), filtered with the band pass filter (not shown), and sampled by an analog-to-digital converter 142. Since the filter 120 is rotating (at approximately 78.125 revolutions per second in one actual embodiment, although other rotational rates could be advantageous as called for by the particular application), samples of the electrical signal output by the detector 140 are indicative of the light intensity detected at various rotational positions of the filter 120. In one advantageous embodiment, one complete rotation (i.e., 360°) of the filter 120 corresponds to 512 digital samples. That is, 512 samples are taken within the period corresponding to one revolution of the filter 120. Thus, for example, if the filter 120 rotates at 78.125 revolutions per second, then 512 samples will be taken within approximately 1/78th of a second, so that the sampling rate of the analog-to-digital converter 142 will be approximately 40,000 samples per second.

As described, the filter 120 constructed in accordance with the present invention includes redundant regions within an entire revolution. Specifically, the filter 120 is symmetrically layered so that the first half-revolution of the filter provides a mirror of the signal of the second half-revolution of the filter 120. That is to say, as depicted in FIG. 2, the filter is formed in a wedge shape so that the thickness in one direction is constant and the thickness in the perpendicular direction increases linearly. Thus, the second half-revolution of the filter 120 is redundant. For this reason, digital samples taken for one-half of the revolution of the filter 120 could be discarded so that in each rotation of the filter 120 there are 256 samples used for purposes of digital signal processing rather than 512 samples in the embodiment described above. Alternatively, all 512 samples can be used for processing by averaging corresponding values. In yet an alternative embodiment, the redundant half of the filter may be used for filter and source calibration. Each of the 256 samples (if only half are used) represents a different portion of the filter 120 having different optical transmission characteristics.

Advantageously, the filter 120 is specially designed to include an opaque strip (i.e., the brass strip 122). The digital signal processor 145 detects when the opaque strip 122 of the filter 120 is interposed between the light 115 and the detector 140 by monitoring the intensity output from the detector 140. This intensity is effectively zero when the light is blocked by the opaque strip 122. Since the opaque strip 122 blocks substantially all of the optical radiation transmitted from the source 110, any signal output from the optical detector 140 when the light is blocked (e.g., from ambient light, thermal effects, etc.), will be interpreted as electrical noise which is not due to either the spectral absorption characteristics of the medium under test 131 or the spectral transmission characteristics of the filter 120. Thus, the digital signal processor 145 interprets the signal present at the output of the optical detector 140 when the brass strip 122 is interposed between the light source 110 and the optical detector 140 as stochastic noise which is subsequently subtracted from all signals output from the optical detector 140. In one embodiment, this is simply accomplished by subtracting the digital value corresponding to the detected noise level from each of the digital values corresponding to the detected signal samples obtained within the activity block 315. Alternatively, a shutter mechanism could be interposed within the light path, or the lamp 110 could be turned off momentarily to provide the same effect. In this manner, the electrical noise inherent within the system is removed so that those electrical signals due to the optical transmission characteristics of the filter 120 (and the test medium 130) are considered in the further processing steps.

Once the stochastic noise inherent within the system has been extracted, control passes from the activity block 315 to an activity block 323. Within the activity block 323 the signal is divided by $I_o$ to normalize the signal. The normalized signal is subsequently processed within an activity block 325 to construct a signal intensity matrix, or vector, from the sample values obtained within the activity block 315 (taking into consideration the subtraction of the electrical noise, and the signal normalization performed in the activity block 323) FIG. 8 illustrates a signal intensity matrix $I_{\phi m}$.

The signal intensity matrix 1000 (FIG. 8) is a one column matrix (sometimes referred to as a vector) including 256 signal intensity values (e.g., one value for each sampled rotational position of the filter 120 in the present embodiment). Thus, the signal intensity vector 1000 is obtained by direct measurement of the optical signal which passes through both the filter 120 and the test medium 131 and is detected by the optical detector 140. Of course, the values used to form the signal intensity vector 1000 are taken from the amplitude of the signals output from the detector 140 after subtraction of the noise from each sample. Designating each rotational position of a filter 120 which is sampled by the analog-to-digital converter 170 by the symbol $\phi$, then $\phi_1$ will correspond to the first rotational position of the filter 120, $\phi_2$ will correspond to the second rotational position of the filter 120, to $\phi_{256}$, which corresponds to the last rotational position of the filter 120 before $\phi_1$ is taken again. Using this notation, $I_{\phi 1}$ corresponds to the intensity of light detected by the optical detector 140 when the filter 120 is in the first rotational position $\phi_1$, $I_{100\ 2}$ corresponds to the intensity of light detected by the detector 140 when the filter 120 is in the second rotational position $\phi_2$, etc. Thus, the signal intensity matrix comprises a single column matrix having 256 digital values from $I_{100\ 1}$ to $I_{\phi 256}$, which correspond to the optical intensities detected at each of the rotational positions of the filter 120. In one embodiment, the intensity values for several revolutions are averaged to form the signal intensity matrix.

Once the signal intensity vector has been obtained activity block 325 (FIG. 6), hereinafter designated as $I(\phi)$, and the filter characteristics matrix, hereinafter designated as $F(\phi,\lambda)$, has been obtained as explained above and represented as a data input in a block 333, the signal intensity matrix together with the filter characteristics matrix may be used to obtain a matrix indicative only of the optical absorption characteristics of the test medium 131, as represented in activity blocks 330, 331. That is, since the overall optical absorption is known as measured within the signal intensity matrix, $I(\phi)$, and the optical transmission characteristics of the filter 120 are known as represented by the filter characteristics matrix, $F(\phi,\lambda)$ the optical absorption of the detected light due to the characteristics of the test medium 131 may be determined by removing the optical transmission characteristics due to the filter from the overall intensity vector $I(\phi)$ combined. This is accomplished by first taking the inverse transform of the filter matrix, as represented in the activity block 331, and subsequently multiplying the signal intensity vector $I(\phi)$ by the inverse filter matrix, as represented in the activity block 330.

If the transmission through the test medium 131 is designated as $T(\lambda)$ wherein the transmission of light through the test medium 131 is defined as a function of the wavelength, and the transmission of light through a selected rotational position (e.g., when $\phi=0$, corresponding to 0°) of a filter 120 is maintained as a function of wavelength and is designated by the function $F(\phi,\lambda)$, the combination, or convolution, of the optical absorption due to the test medium 131 and the filter 120 is designated over the same wavelengths by the function $I(\phi)$. To obtain $T(\lambda)$ from the intensity vector $I(\phi)$ and the filter transmission matrix $F(\phi,\lambda)$, the intensity vector $I(\phi)$ and the inverse $F^{-1}(\phi\lambda)$ are multiplied.

The functions $I(\phi)$ and $F(\phi,\lambda)$ may be represented by the signal intensity and filter characteristic matrices, respectively. Thus, since $$I(\phi) = F(\phi,\lambda) \times T(\lambda) \quad (1)$$

and $I(\phi)$ represents a one-column matrix (vector) containing an intensity value for each rotational position value $\phi$, while $F(\phi,\lambda)$ represents a two dimensional matrix containing a filter transmission coefficient value for each value of $\phi$ and each value of $\lambda$ (FIG. 4D), then the function $T(\lambda)$, representative of optical transmission through the test medium 131, may be represented as a one column matrix having values for each of the various wavelength values, $\lambda$.

In accordance with one embodiment of the present invention, 16 wavelengths are selected over the range of 850 nanometers to 1,400 nanometers for purposes of characterizing the spectral characteristics of the test medium 131 as well as the filter 120.

The matrix form of equation (1) above is shown below:

$$I(\phi) \qquad F(\phi, \lambda) \qquad T(\lambda) \qquad (2)$$

$$\begin{bmatrix} I_{\phi 1} \\ I_{\phi 2} \\ \vdots \\ I_{\phi m} \end{bmatrix} = \begin{bmatrix} f_{\phi 1 \lambda 1} & f_{\phi 1 \lambda 2} & \cdots & f_{\phi 1 \lambda n} \\ f_{\phi 2 \lambda 1} & \ddots & \cdots & \vdots \\ \vdots & \vdots & \cdots & \vdots \\ f_{\phi m \lambda 1} & \cdots & \cdots & f_{\phi m \lambda n} \end{bmatrix} \cdot \begin{bmatrix} t_{\lambda 1} \\ t_{\lambda 2} \\ \vdots \\ t_{\lambda n} \end{bmatrix}$$

As shown in Equation (2), the signal intensity matrix $I(\phi)$ is equal to the product of the two dimensional filter characteristic matrix, $F(\phi,\lambda)$, and the single column test medium matrix $T(\lambda)$. In this equation, two of the matrices are given (i.e., $I(\phi)$ and $F(\phi,\lambda)$). Thus, the third matrix, $T(\lambda)$, which represents the optical transmission characteristics of the test medium 131 for the 16 selected wavelengths between 850 nanometers and 1,400 nanometers, may be obtained by simply multiplying the inverse of the filter characteristic matrix, designated as $F^{-1}(\phi,\lambda)$, by the signal intensity matrix, I(φ), using conventional matrix inversion and multiplication techniques, as shown below.

$$\begin{array}{ccc} T(\lambda) & F^{-1}(\phi,\lambda) & I(\phi) \\ \begin{bmatrix} t_{\lambda 1} \\ t_{\lambda 2} \\ \vdots \\ t_{\lambda N} \end{bmatrix} = \begin{bmatrix} f_{\phi 1 \lambda 1} & f_{\phi 2 \lambda 2} & f_{\phi 1 \lambda m} \\ f_{\phi 2 \lambda 1} & \ddots & \vdots \\ \vdots & \vdots & \vdots \\ f_{\phi m \lambda 1} & \cdots & f_{\phi m \lambda n} \end{bmatrix}^{-1} \cdot \begin{bmatrix} I_{\phi 1} \\ I_{\phi 2} \\ \vdots \\ I_{\phi m} \end{bmatrix} \end{array} \quad (3)$$

Thus, as indicated in an activity block 331, the inverse transform is taken of the filter characteristic matrix, $F^{-1}(\phi, \lambda)$, and then this inverse matrix is multiplied by the signal intensity matrix, I(φ), within the activity block 330 to obtain the frequency response of the test medium 131 as expressed by the test medium characteristic matrix, or transmission vector T(λ).

FIG. 8 illustrates this operation in pictorial form. As shown in FIG. 8, the light source 110 emits light which passes through the lens 117 and the filter 120 to provide filtered optical radiation 125. The optical radiation 125 passes through the medium under test 131 to provide an optical signal used to generate the signal intensity matrix 1000.

The signal intensity matrix 1000 is multiplied by the inverse of the filter characteristic matrix 1010 as indicated within a block 1005. As shown in FIG. 9, the filter characteristic matrix 1010 is derived from an analysis of the filter 120, as described above. The inverse transform of the filter characteristic matrix 1010 is multiplied by the signal intensity vector 1000 to obtain the optical frequency response matrix, or transmission vector, 1015.

Further processing depends on the desired analysis of the test medium.

APPLICATIONS OF THE FILTER

The optical filter of the present invention has uses in various applications. In practice, the optical filter could be used with any applications where optical radiation is distinguished into multiple spectra. For example, particular benefits of the invention may be exhibited in on-line, in-stream chemical process analyzers, or industrial applications where fast, small, low-cost instruments are needed. It should be noted that the circular scanning technique used with a rotating dichroic filter provides a significant mechanical advantage which provides for an increased scanning speed over linear sinusoidal oscillation or a sawtooth scan. Thus, the polychrometer filter wheel 120 has many applications in the process control industry, where rapid, real-time spectra are desired for on-line process control. Specific applications include petroleum distillation processes where different proportions of hydrocarbons are to be determined, drug and alcohol in vivo blood testing, etc.

APPLICATIONS INVOLVING BLOOD GLUCOSE MONITORING

One particularly advantageous application of the filter of the present invention involves monitoring blood glucose levels within a patient, such as a diabetic, without requiring the extraction of blood. This application is described briefly below.

FIG. 3 schematically depicts the filter 120 in operation as an optical filter within a blood glucose monitor. Optical radiation 115 emitted from a light source 110 is focused via a lens assembly 117 (which may comprise fiber optics or the like) and passes through the filter 120. The dichroic filter 120 comprises an optically transmissive rotatable disk substrate which is layered with optical coatings having different thicknesses so as to modulate the broadband optical radiation 115 through a spectrum from the near infrared (NIR) (e.g., 700 nm) to the infrared (IR) (e.g., 1,400 nm). The filter 120 further includes the optically opaque strip 122 which may, for example, comprise brass or some other metal which is deposited radially outward from the center of the filter disk 120. The opaque strip provides a "0" location indicator and zero optical intensity, or electrical offset. The filter disk 120 is driven in a circular motion by a smooth, disk drive motor in one preferred embodiment; however, a stepper motor could be used advantageously for its known phase condition. Filtered optical radiation 125 passes from the filter 120 through a fleshy medium, perfused with blood such as a finger tip 130. In some applications, it may be desirable to provide a focusing lens, or other optical conduit, between the filter 120 and the finger 130. The light which passes through the finger 130 is detected by a detector 140. In general, the detection signal is conditioned and converted to digital form in the analog to digital conversion circuit 142. The digital signal processor 145 accepts the digital signals and accommodates for the imprecision in the dichroic filter.

In operation, when light 115 is emitted from the broadband light source 110 over a wavelength range of approximately 700 nanometers to 1,400 nanometers, (or 850–1700 nanometers in another embodiment where the upper and lower wavelengths have a ratio of approximately 2:1) this broadband light 115 shines through the rotating dichroic filter 120. It should be noted that the light 115 is focused onto a portion of the filter 120 by means of fiber optics, a lens assembly (e.g., the lens 117), or the like. As the dichroic filter 120 rotates, the broadband light 115 is filtered through a portion of the dichroic filter 120 producing the filtered optical radiation 125. As indicated above, the dichroic filter 120 is coated with optical layers of varying thickness so that different portions of the dichroic filter 120 pass different wavelengths of light. Thus, as the filter 120 rotates, the optical radiation 125 output from the filter includes optical radiation of various wavelengths. In one embodiment, a fiber optic is used to couple the optical radiation 125 emitted from a portion of the filter 120 to the patient's finger 120. It should be noted here, that since the optical characteristics of the filter 120 can be carefully measured and the rotational speed of the dichroic filter 120 is known, the time-varying pattern of optical radiation 125 emitted from the filter 120 to illuminate the finger 130 is well defined, and therefore, may be used during signal processing to determine the amount of attenuation which is due to the optical filter 120.

The optical radiation 125 which is used to illuminate the finger 130 passes through the finger 130 to produce the detectable light 135. As is well known in the art, some of the optical radiation 125 passes unimpeded through the finger 130, some of the optical radiation 125 is reflected within the finger 130 to produce scattering. The scattered radiation which is transmitted through the finger 130, together with the light which passes unimpeded through the finger 130, make up the light 135. Some of the optical radiation 125 is absorbed by constituents within the finger 130.

The finger 130 is known to include a fingernail, skin, bones, flesh, and blood. The blood itself primarily comprises water, oxyhemoglobin, hemoglobin, lipids, protein and glucose. Each of these constituents within the finger (e.g., nerves, muscle tissue, etc.) contribute to the absorption and scattering of the optical radiation 125 through the finger 130. The absorption of optical radiation through a nonhomogeneous medium typically follows well defined laws in relation to the optical characteristics of each of the constituents taken separately. Approximations to these laws are expressed in the equations for Beer-Lambert's law, where low scattering applications most closely follow the Beer-Lambert equations. The light 135 which passes through the finger 130 is incident upon the optical detector 140. The optical detector 140 generates an electrical signal proportional to the overall intensity of the light 135.

Although the light 135 typically has different intensities at different wavelengths, the optical detector 140 generates an electrical signal which is proportionate to the area contained under the spectral response curve of the light 135 within the optical band detected by the detector 140. That is, the optical detector 140 receives light having different intensities at different wavelengths. The detected wavelengths are restricted over a band of approximately 850 nm to 1,700 nm due to the characteristics of the detector 140, so that, if intensity is plotted as a function of wavelength to obtain a spectral response curve, the area under the spectral response curve will be indicative of the average optical radiation intensity incident upon the detector 140. Thus, the electrical signal produced by the detector 140 is proportional to the overall (i.e., average) intensity of the light 135.

The filter 120 constructed in accordance with the present invention includes redundant regions within an entire revolution. Specifically, the filter 120 is symmetrically layered so that the first half-revolution of the filter is substantially symmetrical to the signal of the second half-revolution of the filter 120. That is to say, as depicted in FIG. 2, the filter is formed in a wedge shape so that the thickness in one direction is constant and the thickness in the perpendicular direction increases linearly. Thus, the second half-revolution of the filter 120 is redundant. For this reason, digital samples taken for one-half of the revolution of the filter 120 could be discarded so that in each rotation of the filter 120 there are 128 samples used for purposes of digital signal processing rather than 256 samples in one embodiment. Of course, it will be appreciated that some of the samples are lost due to the opaque strip. Alternatively, all 256 samples can be used for processing by averaging corresponding values. In yet an alternative embodiment, the redundant half of the filter may be used for filter and source calibration. Each of the 128 samples (if only half are used) represents a different portion of the filter 120 having different optical transmission characteristics.

This application of the optical filter of the present invention is described in a copending U.S. Patent application entitled "BLOOD GLUCOSE MONITORING SYSTEM," Ser. No. 08/479,164, now U.S. Pat. No. 5,743,262. assigned to the assignee of the present application. The aforementioned application is hereby incorporated by reference. The incorporated patent application also provides additional details about the signal processing steps taken to account for the reduced resolution of the optical filter.

PRODUCTION SPECIFICATIONS FOR THE OPTICAL FILTER

In one advantageous embodiment for blood glucose measurement, the production specifications for the filter 120 are as follows:

SIZE: 20 mm wide×20 mm wavelength span, linear multilayer coating

SUBSTRATE: 25 mm OD glass disc with 7.5 mm shaft hole in center

WAVELENGTH PASSED: 700–1400 nanometers

½ BANDWIDTH: 50 to 200 nanometers, bands may repeat

BLOCKING: none

ENVIRONMENT: Survive condensing humidity, 0–70° C.

The pass band edges are produced so as to differentiate a 20 nanometer band edge.

The pass band may repeat within the window at as little as 400 $cm^{-1}$ spacing, or 17–18 periods within the window. The pass band center transmission should approach 100%, and the region between pass bands should approach 100% reflection.

Blocking requirements outside of the window are not critical. They may be limited by band-edge materials such as RG660, RG700, or semiconductors, or O—H bands typically found in glass below 7100 $cm^{-1}$.

Only the ability to resolve wave number bands near 200 $cm^{-1}$ with one or more band edges should limit the cost.

CHARACTERISTICS FOR PRESENT EMBODIMENT

Preferably, the filter will not have a window narrower than 8,000 to 11,000 $cm^{-1}$ or about 910 to 1,250 nm. The bandwidth is advantageously wider than 200 $cm^{-1}$, and the band edge is advantageously narrower than 200 $cm^{-1}$. The transmission maximum of the primary band is advantageously above 80%, and the transmission minimum is advantageously below 20%. Any other bands should be repeatable, unit to unit; but if they are not, a calibration R$\phi$M could be used in accordance with the DSP to perform initial calibration of individual filters.

MECHANICAL BOUNDARIES AND CHARACTERISTICS FOR THE PRESENT EMBODIMENT

The linear filter is advantageously rotated about its center at less than 4,800 RPM for portable in vivo applications (although near 48,000 RPM might be suitable in certain industrial applications), with an aperture centered at a radius of minimum 9 mm to maximum 45 mm, with a clear aperture diameter of 1 mm to 3 mm and a numerical aperture of 0.12 to 0.40. The light path passes through a small circular portion traveling along an annular region of the rotating filter, causing a sinusoidal scan of the wavelengths, although they are deposited linearly.

For dynamic balance and low turbulence, the linear filter is deposited on a circular substrate. Since the center is not used optically, a standard diameter shaft mounting hole is preferred; most of the present hardware in the invention use either 0.5000–0.000, +0.0005" diameter, or 7.5–0.0+0.1 mm. For a small filter, e.g., 20 mm diameter, bonding to the uncoated side would be considered. Note that the filter mount does not have spokes or other structural interruption of the optical path.

Initial optical-mechanical alignment of the coating on the glass is not critical beyond 0.5 mm and will be established electronically. Some marking of the deposit alignment at the edge or center is desired.

Although the preferred embodiment of the present invention has been described and illustrated above, those skilled in the art will appreciate that various changes and modifications to the present invention do not depart from the spirit of the invention. Accordingly, the scope of the present invention is limited only by the scope of the following appended claims.

What is claimed is:

1. A low cost optical filter comprising:

a generally circular substrate having a surface and plurality of rotational positions around said surface; and a plurality of optical coatings deposited on said surface, said plurality of optical coatings providing transmission characteristics as a function of wavelength and said rotational positions, said transmission characteristics including a plurality of passbands for each of a plurality of wavelengths, and wherein said transmission characteristics include multiple passbands at a plurality of said rotational positions.

2. The optical filter according to claim 1, wherein approximately one-half of the incident light is transmitted through said coatings at said each of said plurality of rotational positions.

3. The optical filter of claim 2, wherein the filter is coupled to a signal processor of which accommodates multiple passbands at the rotational positions on the filter.

* * * * *